United States Patent
Takahashi et al.

(10) Patent No.: US 8,420,873 B2
(45) Date of Patent: Apr. 16, 2013

(54) PROCESS FOR PREPARING 2,3,3,3-TETRAFLUOROPROPENE

(75) Inventors: Kazuhiro Takahashi, Settsu (JP); Takehiro Chaki, Settsu (JP); Yuko Shiotani, Settsu (JP)

(73) Assignee: Daikin Industries, Ltd., Osaka (JP)

( * ) Notice: Subject to any disclaimer, the term of this patent is extended or adjusted under 35 U.S.C. 154(b) by 59 days.

(21) Appl. No.: 13/059,740

(22) PCT Filed: Aug. 20, 2009

(86) PCT No.: PCT/JP2009/064893
§ 371 (c)(1),
(2), (4) Date: Feb. 18, 2011

(87) PCT Pub. No.: WO2010/021406
PCT Pub. Date: Feb. 25, 2010

(65) Prior Publication Data
US 2011/0152585 A1  Jun. 23, 2011

Related U.S. Application Data

(60) Provisional application No. 61/091,030, filed on Aug. 22, 2008.

(51) Int. Cl.
*C07C 17/00* (2006.01)
(52) U.S. Cl.
USPC .............................. 570/202; 570/155; 570/156
(58) Field of Classification Search .................. 570/155, 570/156, 202
See application file for complete search history.

(56) References Cited

U.S. PATENT DOCUMENTS

| | | | |
|---|---|---|---|
| 7,678,949 B2 | 3/2010 | Rao et al. | |
| 7,722,781 B2 | 5/2010 | Rao et al. | |
| 2008/0058562 A1 | 3/2008 | Petrov et al. | |
| 2008/0207964 A1* | 8/2008 | Rao et al. | 570/169 |
| 2009/0118554 A1 | 5/2009 | Rao et al. | |
| 2009/0127496 A1 | 5/2009 | Rao et al. | |
| 2010/0185029 A1 | 7/2010 | Elsheikh et al. | |
| 2010/0200798 A1 | 8/2010 | Rao et al. | |

FOREIGN PATENT DOCUMENTS

| WO | 2007/019355 | 2/2007 |
|---|---|---|
| WO | 2008/002500 | 1/2008 |
| WO | 2008/030440 | 3/2008 |
| WO | 2009/003157 | 12/2008 |

OTHER PUBLICATIONS

International Search Report issued Oct. 16, 2009 in International (PCT) Application No. PCT/JP2009/064893.
PCT Written Opinion of the International Searching Authority issued Oct. 16, 2009 in International (PCT) Application No. PCT/JP2009/064893.

\* cited by examiner

*Primary Examiner* — Jafar Parsa
(74) *Attorney, Agent, or Firm* — Wenderoth, Lind & Ponack, L.L.P.

(57) ABSTRACT

The present invention provides a process for producing 2,3,3,3-tetrafluoropropene including the step of dehydrofluorinating 1,1,1,2,3-pentafluoropropane, wherein 1,3,3,3-tetrafluoropropene and 1,1,3,3,3-pentafluoropropane are supplied together with 1,1,1,2,3-pentafluoropropane to a reactor containing a catalyst to simultaneously perform dehydrofluorination reaction and isomerization reaction.

According to the process of the present invention, 2,3,3,3-tetrafluoropropene (HFO-1234yf) can be efficiently produced by effectively using the by-products of the dehydrofluorination reaction.

5 Claims, 1 Drawing Sheet

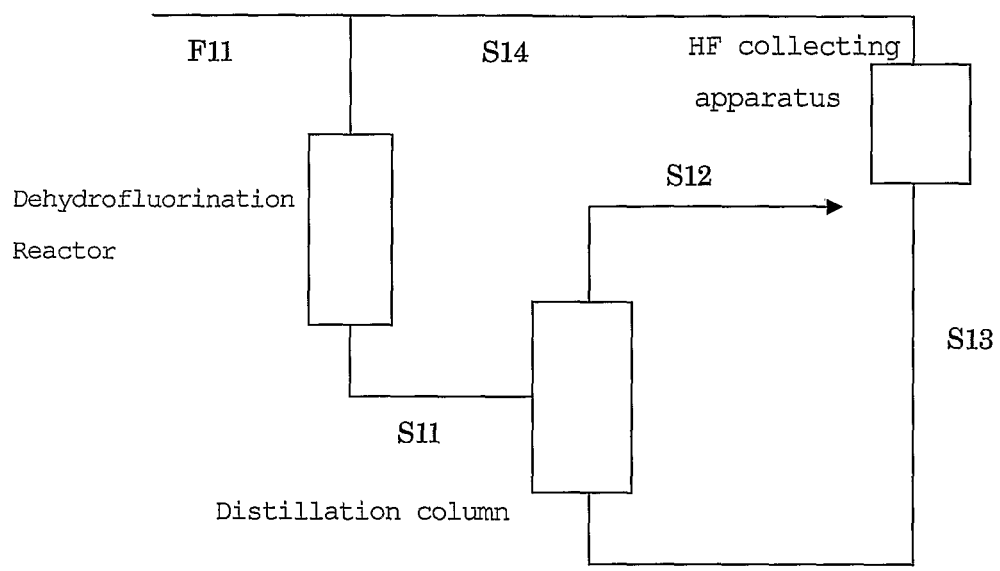

PROCESS FOR PREPARING 2,3,3,3-TETRAFLUOROPROPENE

This application claims priority based on U.S. Provisional Application No. 61/091,030 filed Aug. 22, 2008.

TECHNICAL FIELD

The present invention relates to a process for preparing 2,3,3,3-tetrafluoropropene.

BACKGROUND ART

HFC-125 ($C_2HF_5$), HFC-32 ($CH_2F_2$) and like alternative refrigerants are widely used as vital alternatives for CFCs, HCFCs, etc., which deplete the ozone layer. However, these alternative refrigerants exhibit strong greenhouse effects, and their diffusion may enhance the effects of global warming. As a countermeasure, HFC-125 ($C_2HF_5$), HFC-32 ($CH_2F_2$), etc., are recovered after use, but it is impossible to recover them completely. In addition, the diffusion thereof due to leakage, etc., cannot be ignored. The use of $CO_2$ or hydrocarbon-based materials as an alternative is also under consideration. However, because $CO_2$ refrigerants are inefficient, equipment using such refrigerants inevitably becomes large, causing problems in the comprehensive reduction of greenhouse gas emissions when energy consumption is also considered. Hydrocarbon-based materials are highly combustible and therefore pose safety problems.

2,3,3,3-Tetrafluoropropene (HFO-1234yf, $CF_3CF=CH_2$), which is an olefinic HFC having a low global warming potential, is currently attracting public attention as a substance that can solve these problems.

HFO-1234yf can be produced by using 1,1,1,2,3-pentafluoropropane (HFC-245eb) as a starting material and subjecting the material to dehydrofluorination in the presence of a catalyst. This is the predominant method for obtaining HFO-1234yf at a high yield. Patent Literature (PLT) 1 listed below, for example, discloses a process for preparing 2,3,3,3-tetrafluoropropene (HFO-1234yf), wherein HFC-245eb is subjected to dehydrofluorination in the presence of an alumina catalyst.

However, when HFC-245eb is subjected to the dehydrofluorination reaction, 1,3,3,3-tetrafluoropropene (HFO-1234ze), 1,1,1,3,3-pentafluoropropane (HFC-245fa) and like by-products are produced in addition to the objective 2,3,3,3-tetrafluoropropene (HFO-1234yf), and unreacted HFC-245eb may also remain. Therefore, in order to economically produce 2,3,3,3-tetrafluoropropene (HFO-1234yf), the effective use of these components is desired.

CITATION LIST

Patent Literature

PTL 1: WO2008/2500

SUMMARY OF INVENTION

Technical Problem

The present invention was made in view of the above-described prior art problems. A principal object of the invention is to provide a process for producing 2,3,3,3-tetrafluoropropene (HFO-1234yf) by subjecting 1,1,1,2,3-pentafluoropropane (HFC-245eb) to dehydrofluorination, wherein 2,3,3,3-tetrafluoropropene (HFO-1234yf) can be efficiently produced by effectively using the by-products, etc.

Solution to Problem

The present inventors conducted extensive research to achieve this object. Consequently, the inventors found that, during the dehydrofluorination of 1,1,1,2,3-pentafluoropropane (HFC-245eb), a chromium oxide or a fluorinated chromium oxide effectively functions as a dehydrofluorination catalyst and also exhibits a high catalytic activity in the production of 2,3,3,3-tetrafluoropropene (HFO-1234yf) by the isomerization reaction of a by-product, 1,3,3,3-tetrafluoropropene (HFO-1234ze) and also in the production of 1,3,3,3-tetrafluoropropene (HFO-1234ze) by the dehydrofluorination reaction of a by-product, 1,1,1,3,3-pentafluoropropane (HFC-245fa).

Further, the present inventors found a novel process for effectively producing HFO-1234yf, wherein during the dehydrofluorination of HFC-245eb conducted using a reactor containing a chromium oxide or a fluorinated chromium oxide therein, the dehydrofluorination of HFC-245eb and the isomerization reaction of HFO-1234ze simultaneously proceed by supplying by-produced HFO-1234ze, etc. together with HFC-245eb (starting material) to the reactor. The present invention has thus been accomplished based on this finding.

Specifically, the present invention provides the processes of producing 2,3,3,3-tetrafluoropropene as below.

Item 1. A process for producing 2,3,3,3-tetrafluoropropene comprising the step of dehydrofluorinating 1,1,1,2,3-pentafluoropropane,
wherein 1,3,3,3-tetrafluoropropene and 1,1,3,3,3-pentafluoropropane are supplied together with 1,1,1,2,3-pentafluoropropane to a reactor containing a catalyst to simultaneously perform dehydrofluorination reaction and isomerization reaction.

Item 2. The process according to Item 1, wherein 1,3,3,3-tetrafluoropropene and 1,1,3,3,3-pentafluoropropane supplied to the reactor are by-products of the dehydrofluorination reaction of 1,1,1,2,3-pentafluoropropane.

Item 3. The process according to Item 1, which comprises the steps of:
supplying 1,1,1,2,3-pentafluoropropane in a reactor containing a catalyst therein to conduct a dehydrofluorination reaction;
subjecting the reaction product to distillation to separate the reaction product into a first stream containing 2,3,3,3-tetrafluoropropene as a main component and a second stream containing 1,3,3,3-tetrafluoropropene and 1,1,3,3,3-pentafluoropropane as main components; and
supplying 1,3,3,3-tetrafluoropropene and 1,1,3,3,3-pentafluoropropane obtained from the second stream to the reactor together with 1,1,1,2,3-pentafluoropropane.

Item 4. The process according to Item 1, wherein the catalyst placed in the reactor is a chromium oxide catalyst or a fluorinated chromium oxide catalyst.

Item 5. The process according to Item 1, wherein the catalyst placed in the reactor is a highly fluorinated chromium oxide catalyst having a fluorine content of not less than 30 weight %.

The process of the present invention is explained in detail below.

(1) Starting Material Compound

In the present invention, 1,1,1,2,3-pentafluoropropane (HFC-245eb) is used as the starting material. 1,1,1,2,3-Pentafluoropropane can be synthesized by various methods, for example, a method disclosed in Japanese Patent No. 3158440 wherein 1,1,2,3,3,3-hexafluoropropene is used as the starting material. Hereunder, this method is briefly explained.

1,1,2,3,3,3-Hexafluoropropene used in this method is a compound easy to obtain as a raw material for a resin, etc. By hydrogenating 1,1,2,3,3,3-hexafluoropropene in the presence of a Pd/activated carbon catalyst placed in a reaction tube made of Hastelloy C, 1,1,1,2,3,3-hexafluoropropane (HFC-236ea) can be obtained at a high yield of not less than 98%.

Because the temperature of the catalyst layer rises due to the heat of the reaction, the reaction is usually conducted by supplying an excessive amount of $H_2$, i.e., not less than one mole of $H_2$ per one mole of 1,1,2,3,3,3-hexafluoropropene while cooling the reactor. The reaction temperature is generally about 100 to 400° C., and preferably about 200 to 300° C.

There is no particular limitation to the reaction time, and it can be selected in such a manner that the contact time represented by W/Fo, i.e., the ratio of the weight of the catalyst W (g) relative to the total flow rate $F_o$ (the flow rate: cc/sec at 0° C. and 0.1 MPa) of the starting material gas and hydrogen that are supplied to the reaction system, is generally about 1 to 20 g·sec/cc, and preferably about 4 to 10 g·sec/cc.

Subsequently, hydrogen is separated and the thus-obtained HFC-236ea is subjected to dehydrofluorination, producing 1,2,3,3,3-pentafluoropropene (HFO-1225ye). In this reaction, fluorinated chromium oxide, fluorinated aluminum oxide, fluorinated metals, etc. can be used as a catalyst. Among these, the fluorinated chromium oxide catalyst is particularly preferable.

The reaction temperature is generally about 200 to 500° C., and preferably about 350 to 450° C.

The contact time represented by W/Fo, i.e., the ratio of the weight of the catalyst W (g) relative to the flow rate Fo (the flow rate: cc/sec at 0° C. and 0.1 MPa) of the starting material gas that is supplied to the reaction system, can be selected from the range of generally about 5 to 100 g·sec/cc, preferably about 10 to 80 g·sec/cc, and more preferably about 20 to 70 g·sec/cc.

1,1,1,2,3-Pentafluoropropane (HFC-245eb) is then obtained by addition reaction of hydrogen to HFO-1225ye in the presence of a Pd/activated carbon catalyst.

The reaction temperature is generally about 100 to 400° C., and preferably about 200 to 300° C.

The contact time represented by W/Fo, i.e., the ratio of the weight of the catalyst W (g) relative to the total flow rate Fo (the flow rate: cc/sec at 0° C. and 0.1 MPa) of the starting material gas and hydrogen that are supplied to the reaction system, can be selected from the range of generally about 0.5 to 20 g·sec/cc, and preferably about 1.5 to 10 g·sec/cc.

Alternatively, 1,1,1,2,3-pentafluoropropane (HFC-245eb) can be produced by a process wherein $CCl_3CHClCH_2Cl$ or a like chlorinated alkane is subjected to a chlorine/fluorine exchange reaction using HF.

(2) Dehydrofluorination of HFC-245eb

The process of the present invention uses 1,1,1,2,3-pentafluoropropane (HFC-245eb) as a starting material and produces 2,3,3,3-tetrafluoropropene (HFO-1234yf) by dehydrofluorination.

The dehydrofluorination reaction of HFC-245eb is as shown below.

Chemical Formula 1

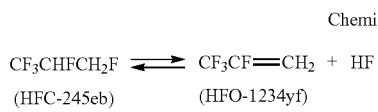

(HFC-245eb)    (HFO-1234yf)

In the present invention, use of a chromium oxide or a fluorinated chromium oxide as a catalyst is essential in the dehydrofluorination reaction of HFC-245eb shown above. According to the studies of the present inventors, it became clear that a chromium oxide catalyst or a fluorinated chromium oxide catalyst exhibits high catalytic activity not only in the above dehydrofluorination reaction but also in the production reaction of 2,3,3,3-tetrafluoropropene (HFO-1234yf) through an isomerization reaction of 1,3,3,3-tetrafluoropropene (HFO-1234ze), which is a by-product produced during the dehydrofluorination reaction of HFC-245eb described later, and in the production of 1,3,3,3-tetrafluoropropene (HFO-1234ze) by the dehydrofluorination reaction of 1,1,1,3,3-pentafluoropropane (HFC-245fa), which is also a by-product produced during the dehydrofluorination reaction of HFC-245eb. Accordingly, in the present invention, by using a chromium oxide or a fluorinated chromium oxide as a catalyst for the dehydrofluorination, by-produced 1,3,3,3-tetrafluoropropene (HFO-1234ze) and 1,1,1,3,3-pentafluoropropane (HFC-245fa) can be efficiently used in a simple production process that is described later.

The chromium oxide and fluorinated chromium oxide used in the present invention are specifically explained below.

There is no limitation to the chromium oxide used in the present invention; however, when the chromium oxide is expressed as $Cr_2O_3 \cdot nH_2O$, n is preferably not greater than 3, and more preferably within the range of 1 to 1.5. It is also preferable to use a chromium oxide represented by the composition formula: $CrO_m$, wherein m falls preferably within the range of $1.5<m<3$, more preferably $2<m<2.75$, and particularly preferably $2<m<2.3$.

The fluorinated chromium oxide catalyst can be prepared by fluorinating a chromium oxide catalyst. The fluorination may be conducted by using HF, fluorocarbon, etc.

The fluorinated chromium oxide catalyst can be prepared by a process, for example, disclosed in Japanese Patent No. 3412165. An example of the process for preparing chromium oxide and an example of the process for preparing a fluorinated chromium oxide catalyst are described below.

First, an aqueous solution of chromium salt (chromium nitrate, chromium chloride, chromium alum, chromium sulfate, etc.) is mixed with aqueous ammonia to form a precipitate of chromium hydroxide. For example, the precipitate of chromium hydroxide can be obtained by adding 10% aqueous ammonia to a 5.7% chromium nitrate solution dropwise in an amount of 1 to 1.2 equivalent weight of ammonia per an equivalent weight of chromium nitrate. The properties of the chromium hydroxide can be controlled by varying the reaction rate during precipitation. A higher reaction rate is preferred. The reaction rate varies depending on the temperature of the reaction solution, procedure for mixing the aqueous ammonia (mixing speed), stirring conditions and the like.

The precipitate is filtered, washed and dried. The drying may be conducted by, for example, air-drying at a temperature of about 70 to 200° C., preferably about 120° C., for about 1 hour to 100 hours, preferably about 12 hours. The product at this stage is herein referred to as a "chromium hydroxide state". Next, the thus-obtained catalyst is then disintegrated into a powder. The rate of precipitation is preferably adjusted in such a manner that the density of the disintegrated powder (for example, having a particle size of not more than 1000 μm, and 95% of the powder having sizes between 46 to 1000 μm) falls within the range of about 0.6 to 1.1 g/ml, preferably a range of about 0.6 to 1.0 g/ml. If the density of the powder is lower than 0.6 g/ml, the strength of the pellets will be undesirably low. On the other hand, if the density of the powder is higher than 1.1 g/ml, the catalyst activity will be low and the pellets are prone to crack. The specific surface area (measured by the BET method) of the powder may preferably be about 100 $m^2$/g or larger, and more preferably about 120 m²/g or larger, after degassing at 200° C. for 80 minutes. The upper limit of the specific surface area is, for example, about 220 m²/g.

If necessary, not more than approximately 3 weight % of graphite is mixed into the thus-obtained chromium hydroxide powder. The resulting mixture is formed into pellets using a tableting machine. The size of the pellets may be about 3.0 mm in diameter and about 3.0 mm in height. The pellets may preferably have a compressive strength (pellet strength) of about 210±40 kg/cm². If the compressive strength is unduly high, the gas contact efficiency decreases to lower the catalyst activity, and the resulting pellets break easily. On the other hand, if the compressive strength is unduly small, the resulting pellets are liable to be powdered, making handling thereof difficult.

The resulting pellets are calcined in an inert atmosphere, for example, in a nitrogen gas stream, giving amorphous chromium oxide. The calcination temperature is preferably not lower than 360° C. However, because chromium oxide is crystallized at exceedingly high temperatures, it is desirable that the calcination temperature be set at the highest possible temperature within the range that the crystallization of chromium oxide is avoidable. For example, the pellets may be calcined at a temperature of about 380 to 460° C., preferably about 400° C., for about 1 hour to 5 hours, preferably about 2 hours.

The calcined chromium oxide may have a specific surface area of not less than about 170 m²/g, preferably not less than about 180 m²/g, and more preferably not less than about 200 m²/g. The upper limit of the specific surface area is generally about 240 m²/g, preferably about 220 m²/g. If the specific surface area is less than 170 m²/g, the catalytic activity becomes undesirably low.

Subsequently, fluorinated chromium oxide can be prepared by subjecting the chromium oxide to fluorination (HF treatment) using hydrogen fluoride. The fluorination temperature may be suitably selected within a range where the water generated does not condense (for example, about 150° C. at 0.1 MPa), and the upper limit may be at a temperature where the catalyst does not crystallize due to the reaction heat. There is no limitation to the pressure during fluorination, but the fluorination is preferably conducted at the pressure at which the catalytic reaction is performed. The fluorination temperature is, for example, in the range of about 100 to 460° C.

In the present invention, it is preferable to use a highly fluorinated chromium oxide catalyst having a high fluorine content. The highly fluorinated chromium oxide catalyst can be obtained by fluorinating a chromium oxide at a higher temperature for a longer time than usual to obtain an ordinary fluorinated chromium oxide catalyst.

The fluorine content of the highly fluorinated chromium oxide catalyst is preferably not less than 30 weight %, and more preferably 30 to 45 weight %. The fluorine content can be measured based on the change in weight of the catalyst or a standard quantitative analysis of chromium oxide. The specific surface area (measured by the BET method) of the highly fluorinated chromium oxide catalyst is generally about 25 to 130 m²/g, and preferably about 40 to 100 m²/g, but not limited to this range.

Dehydrofluorination of HFC-245eb can be conducted by a catalytic reaction in a gas phase. A specific example of the dehydrofluorination process comprises the steps of placing a catalyst in a fixed-bed flow reactor; heating the reactor to the reaction temperature in an electric furnace, etc.; supplying gaseous HFC-245eb (starting material) to the reactor; and passing the HFC-245eb in the reactor. A fixed bed, a fluidized bed, etc. may be used as the contacting means in the gas phase reactor.

In order to prevent the deterioration of the catalyst, about 0.1 to 10 mol % oxygen may be added to the starting material gas.

The reaction temperature is generally about 200 to 500° C., and preferably about 350 to 450° C.

The reaction time is not particularly limited. The degree of conversion can be enhanced by increasing the contact time. However, this increases the amount of catalyst and the size of the equipment, and is thus inefficient. Therefore, it is necessary to select the appropriate contact time.

The contact time represented by W/Fo, i.e., the ratio of the weight of the catalyst used W (g) relative to the flow rate Fo (the flow rate: cc/sec at 0° C. and 0.1 MPa) of the starting material gas that is supplied to the reaction system, is generally about 10 to 80 g·sec/cc, and preferably about 20 to 60 g·sec/cc.

The outflow gas from the reactor contains not only objective HFO-1234yf but also 1,3,3,3-tetrafluoropropene (HFO-1234ze) and 1,1,1,3,3-pentafluoropropane (HFC-245fa) as by-products. The outflow gas may further contain unreacted HFC-245eb. The mechanisms of production of these by-products include not only the direct production from HFC-245eb but also the isomerization reaction of HFO-1234yf and an HF addition reaction as shown below.

Chemical Formula 2

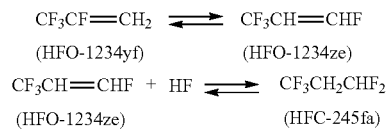

HFO-1234ze has cis-trans isomers (Z)—HFO-1234ze and (E)-HFO-1234ze. In the present invention, both can be used in the same manner.

(3) Recycling Step

In the present invention, the outflow gas form the reactor obtained by the above-described dehydrofluorination reaction may be cooled and liquefied. Thereafter, the liquefied gas may be subjected to distillation and separated into a first stream containing 2,3,3,3-tetrafluoropropene (HFO-1234yf) as a main component and a second stream containing 1,3,3,3-tetrafluoropropene (HFO-1234ze) and 1,1,1,3,3-pentafluoropropane (HFC-245fa) as main components.

The first stream contains not only the objective HFO-1234yf but also HF produced in the dehydrofluorination reaction. Therefore, the objective HFO-1234yf can be obtained by removing HF from the first stream. HF can be removed by washing with water, etc.

After removing HF from the second stream containing 1,3,3,3-tetrafluoropropene (HFO-1234ze) and 1,1,1,3,3-pentafluoropropane (HFC-245fa) as main components and, if necessary, drying it using a molecular sieve or like drying agent, the second stream can be re-supplied to the reactor that is used to conduct the dehydrofluorination together with the HFC-245eb, which is a starting material.

A chromium oxide or a fluorinated chromium oxide is placed in this reactor as a catalyst and the dehydrofluorination of HFC-245eb as a starting material proceeds, producing 2,3,3,3-tetrafluoropropene (HFO-1234yf). 1,3,3,3-Tetrafluoropropene (HFO-1234ze) supplied from the second stream is subjected to an isomerization reaction under the same conditions as those of the dehydrofluorination reaction described above using a chromium oxide or a fluorinated chromium oxide as an isomerization catalyst, and produces 2,3,3,3-tetrafluoropropene (HFO-1234yf). Furthermore, the dehydrofluorination of 1,1,1,3,3-pentafluoropropane (HFC-245fa) supplied from the second stream also proceeds, producing 1,3,3,3-tetrafluoropropene (HFO-1234ze).

Accordingly, the by-products of the dehydrofluorination can be converted into the objective 2,3,3,3-tetrafluoropropene (HFO-1234yf) by separating the outflow gas from the reactor used for the dehydrofluorination reaction into a first stream containing 2,3,3,3-tetrafluoropropene as a main component and a second stream containing 1,3,3,3-tetrafluoropropene and 1,1,1,3,3-pentafluoropropane as main components; and then re-supplying 1,3,3,3-tetrafluoropropene (HFO-1234ze) and 1,1,1,3,3-pentafluoropropane (HFC-245fa) obtained from the second stream to the reactor.

This allows effective use of the by-products to efficiently produce 2,3,3,3-tetrafluoropropene (HFO-1234yf).

Advantageous Effects of Invention

According to the present invention, 2,3,3,3-tetrafluoropropene (HFO-1234yf) can be efficiently produced in a simple process, wherein 1,1,1,2,3-pentafluoropropane (HFC-245eb) is used as a starting material.

BRIEF DESCRIPTION OF DRAWING

FIG. 1 schematically illustrates the process for producing 2,3,3,3-tetrafluoropropene in Example 1.

DESCRIPTION OF EMBODIMENTS

The present invention is explained in detail below with reference to the Examples.

Example 1

(1) Preparation of Highly Fluorinated Chromium Oxide Catalyst

A 10% aqueous ammonia (114 g) was added to a 5.7% chromium nitrate solution (765 g), obtaining a precipitate. The precipitate was filtered, washed, and dried in air at 120° C. for hours, producing chromium hydroxide. The thus-obtained chromium hydroxide was formed into pellets having the size of 3.0 mm in diameter and about 3.0 mm in height. The pellets were then calcined in a nitrogen stream at 400° C. for 2 hours. According to the results of the quantitative analysis of Cr and elemental analysis, the resulting chromium oxide was confirmed to have a composition formula of $CrO_{2.0}$. The pelleted chromium oxide was placed in a reaction tube made of Hastelloy C; hydrogen fluoride was diluted to 20 vol % using nitrogen and supplied to the reaction tube; the tube was heated by increasing the temperature step by step from 200 to 360° C.; and fluorination was then conducted using 100% HF for 220 hours. The resulting fluorinated chromium oxide had a specific surface area (measured by the BET method) of 70 m²/g and the fluorine content was 31.4 weight.

(2) Synthesis of HFC-1234yf

According to the step schematically shown in FIG. 1, 2,3,3,3-tetrafluoropropene (HFC-1234yf) was synthesized in the process described below.

First, 2 kg of highly fluorinated-chromium oxide catalyst prepared in the process described above was placed in a reaction tube made of Hastelloy C, and the temperature of the catalytic layer was maintained at 400° C.

Vaporized 1,1,1,2,3-pentafluoropropane (HFC-245eb) was supplied to this reaction tube at 3 L/min (the flow rate at 0° C. and 0.1 MPa) (stream F11). The starting material carried 3 mol % oxygen. The contact time W/Fo at this time was 40 g·sec/cc. Note that $F_0$ represents the flow rate of HFC-245eb at 0° C. and 0.1 MPa.

The outflow gas (stream S11) from the reaction tube was cooled, and placed in a rectification column having a size of 2 m in height and 7 cm in diameter, a mixture of the objective HFO-1234yf and HF was obtained at the top of the column (stream S12). From the bottom of the column, unreacted HFC-245eb and HFO-1234ze and HFC-245fa as by-products were extracted (stream S13).

The mixture (stream S13) extracted from the bottom of the column was placed in an HF collecting apparatus and washed with water to remove HF, dried using a molecular sieve, re-supplied to the reaction tube (stream S14), and contacted with a highly fluorinated-chromium oxide catalyst along with the HFC-245eb as a starting material under the conditions described above.

Table 1 shows the flow rate (kg/hr) of each component of each stream. Because HFC-245eb (i.e., starting material) was not detected in the outflow gas from the reaction tube, it can be concluded that the conversion rate of HFC-245eb was substantially 100%.

TABLE 1

| | Stream | | | | |
|---|---|---|---|---|---|
| | F11 | S11 | S12 | S13 | S14 |
| | | Flow rate (kg/hr) | | | |
| HFC-245eb | 1.08 | | | | |
| HF | | 0.16 | 0.03 | 0.13 | |
| HFO-1234yf | | 0.92 | 0.92 | | |
| HFO-1234ze | | 0.11 | | 0.11 | 0.11 |
| HFC-245fa | | 0.03 | | 0.03 | 0.03 |

As is clear from Table 1, the flow rate of HFO-1234ze and HFC-245fa (S14) that were re-supplied to the reaction tube was the same as that of the HFO-1234ze and HFC-245fa in the outflow gas (S11) from the reaction tube. In other words, in spite of the continuous reaction, the flow rate of HFO-1234ze and HFC-245fa was maintained at a constant level without increase. From these results, it was confirmed that the by-product from the dehydrofluorination was converted into HFO-1234yf by being re-supplied to the reaction tube. If not recycled, HFO-1234ze and HFC245fa will cause a large loss. By re-supplying HFO-1234ze and HFC245fa (i.e., by-products) to the reaction tube, in which the dehydrofluorination of HFC-245eb is conducted, to use the by-products in the dehydrofluorination reaction and isomerization reaction, the equipment cost and loss of HFO-1234ze and HFC245fa can be reduced.

Example 2

Dehydrofluorination of 1,1,1,2,3-pentafluoropropane (HFC-245eb) and recycling of the by-products were conducted in the same manner as in Example 1 except that HFC-245eb was supplied at 4 L/min (the flow rate at 0° C. and 0.1 MPa, W/Fo=30 g·sec/cc). In this case, the conversion rate of HFC-245eb was substantially 100%. Table 2 shows the flow rate (kg/hr) of each component of each stream.

TABLE 2

| | Stream | | | | |
|---|---|---|---|---|---|
| | F11 | S11 | S12 | S13 | S14 |
| | | | Flow rate (kg/hr) | | |
| HFC-245eb | 1.44 | | | | |
| HF | | 0.21 | 0.03 | 0.12 | |
| HFO-1234yf | | 1.04 | 0.87 | | |
| HFO-1234ze | | 0.15 | | 0.10 | 0.10 |
| HFC-245fa | | 0.04 | | 0.03 | 0.03 |

Example 3

Dehydrofluorination of HFC-245eb and recycling of the by-products were conducted in the same manner as in Example 1 except that the reaction temperature was set at 450° C. In this case, the conversion rate of HFC-245eb was substantially 100%. Table 3 shows the flow rate (kg/hr) of each component of each stream.

TABLE 3

| | Stream | | | | |
|---|---|---|---|---|---|
| | F11 | S11 | S12 | S13 | S14 |
| | | | Flow rate (kg/hr) | | |
| HFC-245eb | 1.08 | | | | |
| HF | | 0.16 | 0.03 | 0.13 | |
| HFO-1234yf | | 0.92 | 0.92 | | |
| HFO-1234ze | | 0.14 | | 0.14 | 0.14 |
| HFC-245fa | | 0.05 | | 0.05 | 0.05 |

The invention claimed is:

1. A process for producing 2,3,3,3-tetrafluoropropene comprising a step of dehydrofluorinating 1,1,1,2,3-pentafluoropropane,
   wherein 1,3,3,3-tetrafluoropropene and 1,1,3,3,3-pentafluoropropane are supplied together with 1,1,1,2,3-pentafluoropropane to a reactor containing a catalyst to simultaneously perform a dehydrofluorination reaction and a isomerization reaction to produce the 2,3,3,3-tetrafluoropropene.

2. The process according to claim 1, wherein the 1,3,3,3-tetrafluoropropene and the 1,1,3,3,3-pentafluoropropane supplied to the reactor are by-products of the dehydrofluorination reaction of 1,1,1,2,3-pentafluoropropane.

3. The process according to claim 1, which comprises the steps of:
   supplying 1,1,1,2,3-pentafluoropropane in a reactor containing a catalyst therein to conduct a dehydrofluorination reaction and obtain a reaction product;
   subjecting the reaction product to distillation to separate the reaction product into a first stream containing 2,3,3,3-tetrafluoropropene as a main component and a second stream containing 1,3,3,3-tetrafluoropropene and 1,1,3,3,3-pentafluoropropane as main components; and
   supplying the 1,3,3,3-tetrafluoropropene and the 1,1,3,3,3-pentafluoropropane obtained from the second stream to the reactor together with the 1,1,1,2,3-pentafluoropropane to produce the 2,3,3,3-tetrafluoropropene.

4. The process according to claim 1, wherein the catalyst in the reactor is a chromium oxide catalyst or a fluorinated chromium oxide catalyst.

5. The process according to claim 1, wherein the catalyst in the reactor is a highly fluorinated chromium oxide catalyst having a fluorine content of not less than 30 weight %.

* * * * *